(12) United States Patent
Thibault et al.

(10) Patent No.: US 6,382,442 B1
(45) Date of Patent: May 7, 2002

(54) PLASTIC CLOSURE FOR VIALS AND OTHER MEDICAL CONTAINERS

(75) Inventors: Jean-Claude Thibault, Saint Egreve; Hubert Jansen, Poisat, both of (FR); Volker Niermann, Little Falls, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/168,502

(22) Filed: Oct. 8, 1998

Related U.S. Application Data

(60) Provisional application No. 60/082,382, filed on Apr. 20, 1998.

(51) Int. Cl.[7] .......................... B65D 39/00; B65D 41/10; B65D 41/28
(52) U.S. Cl. ........................ 215/249; 215/247; 215/251; 215/274; 215/324; 215/325; 215/DIG. 3; 604/411; 604/415
(58) Field of Search ................................. 215/247, 249, 215/251, 274, 317, 321, 320, 324, 325, 327, DIG. 3, 248, 253, 297, 250, 252, 295, 296; 222/81, 83, 83.5; 141/2, 25, 26, 27, 28, 329, 330, 18, 21; 604/403, 406, 411–416; 220/265–268, 278

(56) References Cited

U.S. PATENT DOCUMENTS 37,221 A    12/1862  Dunton (List continued on next page.)

FOREIGN PATENT DOCUMENTS

| EP | 0 236 127 A2 | 3/1987 |
| EP | 0 406 374 B1 | 12/1989 |
| EP | 0 065 469 A2 | 5/1992 |
| EP | 0 769 456 A2 | 10/1996 |
| EP | 0 747 293 A1 | 12/1996 |
| WO | WO 84/04673 | 12/1984 |

(List continued on next page.)

OTHER PUBLICATIONS

French Patent No. 2.738.550, Sep. 9, 1995—translation attached.

(List continued on next page.)

Primary Examiner—Stephen P. Garbe
Assistant Examiner—Niki M. Eloshway
(74) Attorney, Agent, or Firm—Allen W. Mark, Esq.

(57) ABSTRACT

The plastic closure of this invention is particularly, but not exclusively adapted for sealing medicament vials and other medical containers or as a collar for retaining a fluid transferset on a medical container. The plastic closure of this invention includes a generally tubular portion which surrounds the rim of the container and a free end portion which is permanently radially deformed or crimped into the neck of the container. The plastic closure of this invention is formed of a polymer, preferably a polymeric alloy or melt blend, which is sufficiently malleable to permit radial deformation, yet sufficiently rigid to retain its shape following deformation and sufficiently resistant to creep to maintain the seal between the plastic closure and the container following deformation. A preferred polymer for the plastic closure of this invention is an alloy or melt blend comprising a relatively rigid polymer such as polycarbonate and a soft malleable co-polymer such as a polyester. Where the plastic closure of this invention is used to seal a vial, for example, the closure includes a radial portion overlying the rim portion of the stopper having a central opening and a cup-shaped cap is received over the collar having retainer portions received within the central opening of the cap which may be removed by finger pressure. When the collar of this invention is used to secure a fluid transferset on a vial, the collar includes a proximate tubular portion integral with the radial portion which surrounds at least a portion of the transferset. In one embodiment, the second tubular portion surrounds the entire transferset and the open end is sealed with a peel-off seal and in another embodiment a separate cap surrounds the distal end of the transferset.

21 Claims, 5 Drawing Sheets

U.S. PATENT DOCUMENTS

| | | | |
|---|---|---|---|
| 659,519 A | 10/1900 | De Oliveria | |
| 1,440,986 A | * 1/1923 | Hammer | 215/327 |
| 2,342,215 A | 2/1944 | Perelson | |
| 2,388,634 A | 11/1945 | DeWoody | |
| 2,524,365 A | 10/1950 | Smith | |
| 2,607,503 A | 8/1952 | Sonnenberg | |
| 2,653,609 A | 9/1953 | Smith | |
| 2,659,370 A | 11/1953 | Smith | |
| 2,667,986 A | 2/1954 | Perelson | |
| 2,708,050 A | * 5/1955 | Luertzing et al. | 215/324 |
| 2,953,132 A | 3/1960 | Richter et al. | |
| 3,033,202 A | 5/1962 | Richter et al. | |
| 3,164,303 A | 1/1965 | Trautmann | |
| 3,206,080 A | 9/1965 | Scislowicz | |
| 3,278,063 A | * 10/1966 | Kranzhoff | 215/303 |
| 3,356,093 A | 12/1967 | Monahon | |
| 3,357,427 A | 12/1967 | Wittke et al. | |
| 3,610,297 A | 10/1971 | Raaf et al. | |
| 3,674,028 A | 7/1972 | Ogle | |
| 3,779,371 A | 12/1973 | Rovinksi | |
| 3,810,469 A | 5/1974 | Hurschman | |
| 3,826,260 A | 7/1974 | Killinger | |
| 3,838,689 A | 10/1974 | Cohen | |
| 3,872,992 A | 3/1975 | Larson | |
| 3,940,003 A | 2/1976 | Larson | |
| 3,977,555 A | 8/1976 | Larson | |
| 3,995,630 A | 12/1976 | Van De Veerdonk | |
| 4,020,839 A | 5/1977 | Klapp | |
| 4,048,999 A | 9/1977 | Kobel | |
| 4,067,440 A | 1/1978 | Lataix | |
| 4,153,057 A | 5/1979 | Kobel | |
| 4,187,893 A | 2/1980 | Bujan | |
| 4,210,255 A | 7/1980 | Pan | |
| 4,296,786 A | 10/1981 | Brignola | |
| 4,336,891 A | 6/1982 | Smith | |
| 4,387,879 A | 6/1983 | Tauschinski | |
| 4,412,623 A | 11/1983 | Schmidt | |
| 4,418,827 A | 12/1983 | Butterfield | |
| 4,425,120 A | 1/1984 | Sampson et al. | |
| 4,460,735 A | * 7/1984 | Froix | 524/537 |
| 4,493,348 A | 1/1985 | Lemmons | |
| 4,505,709 A | 3/1985 | Froning et al. | |
| 4,507,113 A | 3/1985 | Dunlap | |
| 4,564,054 A | 1/1986 | Gustavsson | |
| 4,573,506 A | 3/1986 | Paoletti | |
| 4,573,976 A | 3/1986 | Sampson et al. | |
| 4,576,211 A | 3/1986 | Valentini et al. | |
| 4,588,403 A | 5/1986 | Weiss et al. | |
| 4,619,651 A | 10/1986 | Kopfer et al. | |
| 4,624,393 A | 11/1986 | Lopez | |
| 4,639,250 A | 1/1987 | Rycroft | |
| 4,662,878 A | 5/1987 | Lindmayer | |
| 4,672,996 A | 6/1987 | Floyd et al. | |
| 4,673,404 A | 6/1987 | Gustavsson | |
| 4,675,020 A | 6/1987 | McPhee | |
| 4,792,053 A | 12/1988 | Towne et al. | |
| 4,822,351 A | 4/1989 | Purcell | |
| 4,826,491 A | 5/1989 | Schramm | |
| 4,834,149 A | 5/1989 | Fournier et al. | |
| 4,834,152 A | 5/1989 | Howson et al. | |
| 4,850,994 A | 7/1989 | Zerbet et al. | |
| 4,884,703 A | 12/1989 | O'Meara | |
| 4,909,290 A | 3/1990 | Coccia | |
| 4,913,945 A | * 4/1990 | Maruhashi et al. | 428/36.92 |
| 4,923,447 A | 5/1990 | Morgan | |
| 4,927,423 A | 5/1990 | Malmborg | |
| 4,932,937 A | 6/1990 | Gustavsson et al. | |
| 4,944,736 A | 7/1990 | Holtz | |
| 4,982,740 A | 1/1991 | Broden | |
| 5,006,118 A | 4/1991 | Yule | |
| 5,024,256 A | 6/1991 | Vadjer | |
| 5,035,689 A | 7/1991 | Schroeder | |
| 5,060,812 A | 10/1991 | Ogle, II | |
| 5,088,996 A | 2/1992 | Kopfer et al. | |
| 5,092,840 A | 3/1992 | Healy | |
| 5,116,326 A | 5/1992 | Schmidt | |
| 5,169,385 A | 12/1992 | Turnball | |
| 5,171,214 A | 12/1992 | Kolber et al. | |
| 5,215,538 A | 6/1993 | Larkin | |
| 5,217,433 A | 6/1993 | Bunin | |
| 5,232,029 A | 8/1993 | Knox et al. | |
| 5,232,109 A | 8/1993 | Tirrell et al. | |
| 5,250,037 A | 10/1993 | Bitdinger | |
| 5,275,299 A | 1/1994 | Konrad et al. | |
| 5,279,576 A | 1/1994 | Loo et al. | |
| 5,291,991 A | 3/1994 | Meyer | |
| 5,297,599 A | 3/1994 | Bucheli | |
| 5,342,319 A | 8/1994 | Watson et al. | |
| 5,348,548 A | 9/1994 | Meyer et al. | |
| 5,350,372 A | 9/1994 | Ikeda et al. | |
| 5,352,196 A | 10/1994 | Haber et al. | |
| 5,358,501 A | 10/1994 | Meyer | |
| 5,360,413 A | 11/1994 | Leason et al. | |
| 5,364,386 A | 11/1994 | Fukuoka et al. | |
| 5,385,546 A | 1/1995 | Kriesel | |
| 5,397,303 A | 3/1995 | Sancoff et al. | |
| 5,409,125 A | 4/1995 | Kimber et al. | |
| 5,411,499 A | 5/1995 | Dudar et al. | |
| 5,415,374 A | 5/1995 | Carroll et al. | |
| 5,419,256 A | 5/1995 | Pollich | |
| 5,421,814 A | 6/1995 | Geary | |
| 5,423,791 A | 6/1995 | Bartlett | |
| 5,425,465 A | 6/1995 | Healy | |
| 5,429,256 A | 7/1995 | Kestenbaum | |
| 5,433,330 A | 7/1995 | Yatsko et al. | |
| 5,433,703 A | 7/1995 | Utterberg et al. | |
| 5,435,282 A | 7/1995 | Haber et al. | |
| 5,437,648 A | 8/1995 | Graves et al. | |
| 5,441,487 A | 8/1995 | Vedder | |
| 5,454,409 A | 10/1995 | McAffer et al. | |
| 5,454,805 A | 10/1995 | Brony | |
| 5,466,219 A | 11/1995 | Lynn et al. | |
| 5,470,319 A | 11/1995 | Mayer | |
| 5,470,327 A | 11/1995 | Helgren et al. | |
| 5,474,541 A | 12/1995 | Ritsky et al. | |
| 5,474,544 A | 12/1995 | Lynn | |
| 5,487,737 A | 1/1996 | Meyer | |
| 5,494,170 A | * 2/1996 | Burns | 215/247 |
| 5,501,676 A | 3/1996 | Niedospial et al. | |
| 5,514,116 A | 5/1996 | Vaillancourt et al. | |
| 5,514,117 A | 5/1996 | Lynn | |
| 5,520,641 A | * 5/1996 | Behnke et al. | 604/86 |
| 5,520,642 A | 5/1996 | Bigagli et al. | |
| 5,520,661 A | 5/1996 | Lal et al. | |
| 5,520,665 A | 5/1996 | Fleetwood | |
| 5,520,666 A | 5/1996 | Choudhury et al. | |
| 5,533,983 A | 7/1996 | Haining | |
| 5,533,994 A | 7/1996 | Meyer | |
| 5,549,651 A | 8/1996 | Lynn | |
| 5,566,729 A | 10/1996 | Grabenkort et al. | |
| 5,573,516 A | 11/1996 | Tyner | |
| 5,573,520 A | 11/1996 | Schwartz et al. | |
| 5,573,525 A | 11/1996 | Watson et al. | |
| 5,573,526 A | 11/1996 | Hess | |
| 5,576,392 A | * 11/1996 | Yamamoto et al. | 525/289 |

| | | | |
|---|---|---|---|
| 5,598,939 A | 2/1997 | Watson et al. | |
| 5,613,291 A | 3/1997 | Solomon et al. | |
| 5,616,129 A | 4/1997 | Mayer | |
| 5,616,130 A | 4/1997 | Mayer | |
| 5,620,434 A | 4/1997 | Brony | |
| 5,641,010 A | 6/1997 | Maier | |
| 5,662,230 A | 9/1997 | Finneran | |
| 5,685,845 A | 11/1997 | Grimard | |
| 5,697,915 A | 12/1997 | Lynn | |
| 5,702,019 A | 12/1997 | Grimard | |
| 5,709,666 A | 1/1998 | Reynolds | |
| 5,718,348 A | * 2/1998 | Manera | 215/249 |
| 5,776,124 A | 7/1998 | Wald | |
| 5,776,125 A | 7/1998 | Dudar et al. | |
| 5,785,701 A | 7/1998 | Sams et al. | |
| 5,803,284 A | 9/1998 | Grimard | |
| 5,819,964 A | * 10/1998 | Grimard | 215/249 |
| 5,833,089 A | * 11/1998 | Manni et al. | 215/249 |
| 5,855,575 A | 1/1999 | Solomon et al. | |
| 5,863,655 A | * 1/1999 | Mock | 428/411.1 |
| 5,873,872 A | 2/1999 | Thibault et al. | |
| 5,879,345 A | 3/1999 | Aneas | |
| 5,891,129 A | 4/1999 | Daubert et al. | |
| 5,925,029 A | 7/1999 | Jansen et al. | |
| 5,931,828 A | 8/1999 | Durkee | |
| 5,954,104 A | 9/1999 | Daubert et al. | |
| 5,957,898 A | * 9/1999 | Jepson et al. | 604/256 |
| 6,003,566 A | 12/1999 | Thibault et al. | |
| 6,039,093 A | 3/2000 | Mrotzek et al. | |
| 6,050,435 A | 4/2000 | Bush et al. | |
| 6,056,135 A | 5/2000 | Widman | |
| 6,070,623 A | 6/2000 | Aneas | |
| 6,071,270 A | 6/2000 | Fowles et al. | |
| 6,139,534 A | 10/2000 | Niedospial, Jr. et al. | |

FOREIGN PATENT DOCUMENTS

| | | |
|---|---|---|
| WO | WO 88/01881 | 3/1988 |
| WO | WO 92/11056 | 7/1992 |
| WO | WO 94/03373 | 2/1994 |
| WO | WO 95/00117 | 1/1995 |
| WO | WO 95/03841 | 2/1995 |
| WO | WO 95/14176 | 5/1995 |
| WO | WO 95/31242 | 11/1995 |
| WO | WO 95/33505 | 12/1995 |
| WO | WO 95/35125 | 12/1995 |
| WO | WO 96/13301 | 5/1996 |
| WO | WO 97/00702 | 1/1997 |
| WO | WO 97/10156 | 3/1997 |
| WO | WO 97/39720 | 10/1997 |
| WO | 9739720 | * 10/1997 |
| WO | WO 98/13006 | 4/1998 |
| WO | WO 98/32411 | 7/1998 |
| WO | WO 98/37853 | 9/1998 |
| WO | WO 98/37854 | 9/1998 |

OTHER PUBLICATIONS

French Patent No. 2.395.198, Jan. 19, 1979.
French Patent No. 950.625, Jul. 28, 1947.
French Patent No. 1.071.487, Feb. 26, 1953.
French Patent No. 1.328.635, Jul. 4, 1962.
French Patent No. 1.487.413, May 20, 1966.
German Patent No. DE 36 18 158 A1, May 30, 1986.
Swiss Patent No. 501 172, Dec. 31, 1970.
UK Patent Application No. 2 121 016 A, Jun. 1, 1983.

* cited by examiner

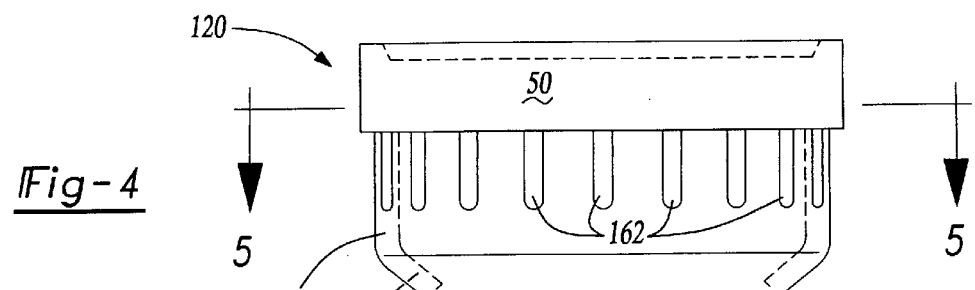
*Fig-4*
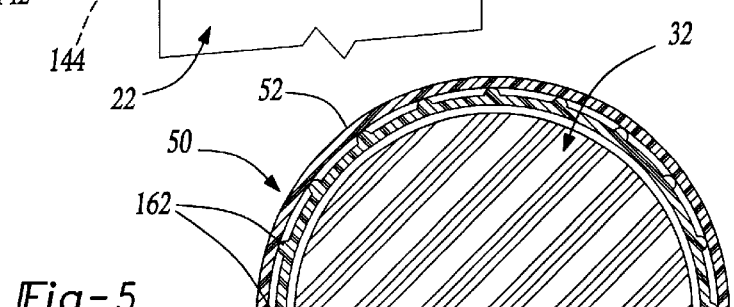
*Fig-5*
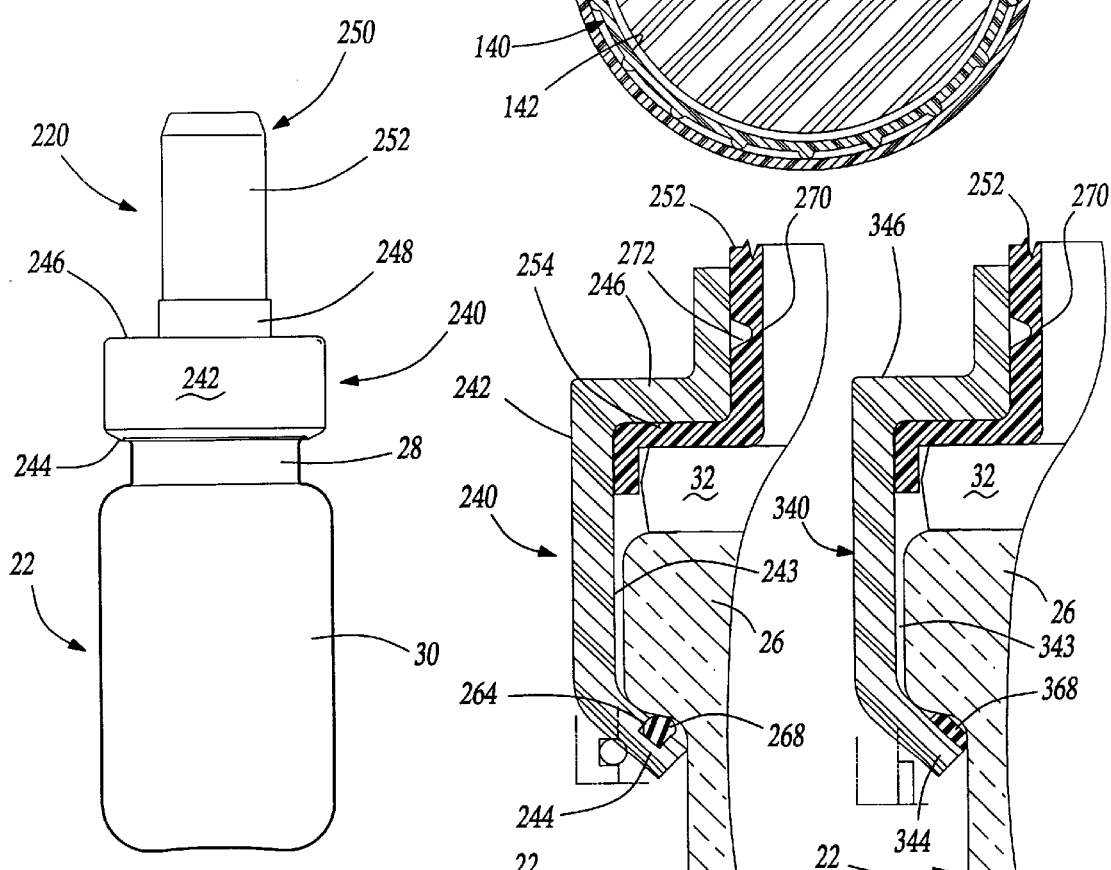
*Fig-6*  *Fig-7*  *Fig-8*

PLASTIC CLOSURE FOR VIALS AND OTHER MEDICAL CONTAINERS

This application claims benefit of U.S. application Ser. No. 60/082,382, filed Apr. 20, 1998.

FIELD OF THE INVENTION

This invention relates to an improved plastic closure such as a cap or collar for closing or sealing containers such as vials containing a medicament which eliminates the problems associated with a malleable metal cap or collar such as aluminum. The plastic closure of this invention may be used as a cap to seal a conventional vial having an elastomeric stopper or as a collar for retaining a fluid transferset separate from or integral with the collar.

BACKGROUND OF THE INVENTION

It is conventional to store medicament such as drugs in a sealed vial or other container for later use. Such medicaments may be in a dry or powdered form to increase the shelf life of the drugs and reduce inventory space. Such dry or powdered drugs are generally stored in a sealed vial and reconstituted in liquid form for administration to a patient by adding a diluent or solvent. Alternatively, the drug may be in liquid or even gaseous form. A conventional vial for storing medicament generally includes an open end, a radial rim portion surrounding the open end and a reduced diameter neck portion adjacent the rim portion. The vial is conventionally sealed with an elastomeric stopper which generally includes a tubular portion inserted into the neck of the vial and a planar rim portion which overlies the vial rim. The stopper is normally secured to the vial with a thin malleable metal cap, such as aluminum. The aluminum cap includes a tubular portion which surrounds the rim portions of the stopper and vial, an inwardly projecting annular portion which overlies the rim portion of the stopper and a distal end portion which is crimped or deformed radially into the vial neck beneath the vial rim portion. Because aluminum is malleable, the collar accommodates the buildup of tolerances of the dimensions of the stopper and vial rim. The dimensions and tolerances of standard vials and stoppers are set by the International Standards Organization (ISO).

The radial portion of the aluminum cap which overlies the stopper rim portion may be closed, in which case the aluminum cap is removed by "peeling" the aluminum cap from the vial. A pre-slit tab located in the middle area is provided which overlies the vial rim, permitting the cap to be torn from the top and peeled from the vial prior to use. This closed embodiment of an aluminum cap has several disadvantages. First, the tearing of the metal cap creates sharp edges which may cut or damage sterile gloves and cut the person administering the drug, thereby exposing both the healthcare worker and the patient to disease and contamination of the drug. Second, the tearing of the aluminum cap generates metal particles which may also contaminate the drug. The dangers associated with the tearing of an aluminum cap has been solved in part by adding a "flip-off" plastic cap. In one such embodiment, the aluminum collar includes a central opening and a shallow plastic cup-shaped cap is received over the aluminum collar having a central projecting riveting portion which is received and secured in the central opening of the aluminum collar. The plastic cap is then removed by forcing the flip-off cap away from the aluminum collar, which tears an annular serrated portion surrounding the central opening and exposes an opening in the collar for receipt of a hypodermic needle or the like. This embodiment reduces but does not eliminate the possibility of tearing the sterile gloves of the healthcare worker. More importantly, however, aluminum dust is still created which may contaminate the medicament. It is also important to note that metallic dust is also created simply by forming and affixing the aluminum collar to the vial because aluminum dust is created in forming the aluminum collar, crimping of the collar and removal of the flip-off plastic cap.

Aluminum collars have also been used to secure a fluid transferset on medicament vials. Transfersets may be utilized, for example, to transfer fluid from a syringe to a vial, such as to reconstitute a dry or powdered drug in a vial by adding a diluent or solvent. The reconstituted drug may then be withdrawn from the vial by the syringe. The inner surface of the transferset may be part of the drug fluid path and the aluminum collar or ring may bring aluminum particles in the sterile room where the drug is added to the vial or into the drug fluid path contaminating the drug. There have been attempts to reduce this problem by applying a coating to the aluminum cap or collar. Finally, the prior art also includes snap-on cup-shaped plastic caps or collars having a radially inwardly projecting end portion which is snapped over the rim portion of the vial. Snap-on plastic collars, however, do not assure adequate sealing of the vial or fully accommodate the tolerances of standard vials and stoppers as required.

The need therefore remains for a closure for vials and other medical containers which may be utilized with conventional containers, such as medicament vials or cartridges, which assures sealing of the container and which achieves a good level of cleanliness, without metal particles or dust which may contaminate the medicament, the transferset or the clean room and which does not expose the healthcare worker to sharp metal edges. The plastic closure of this invention solves these problems and permits the use of the plastic closure of this invention for attaching and sealing containers and fluid transfersets as described below.

SUMMARY OF THE INVENTION

As set forth above, the plastic closure for sealing a vial or other medical container of this invention eliminates the problems associated with a malleable metal or aluminum cap or collar, but which accommodates the buildup of tolerances of the rim portion of the container and the elastomeric stopper, when used. The plastic closure of this invention is relatively inexpensive to manufacture and use. The plastic closure of this invention may be utilized as a cap to seal a conventional medicament vial, as a collar in combination with a flip-off cap or as a collar used to secure and seal a transferset on a vial for transferring fluid between a vial or other container and a second container. As used herein, the term closure is generic to either a cap or collar.

As stated, the plastic closure for sealing a container of this invention may be utilized with a conventional vial having an open end and a reduced diameter neck portion adjacent the open end. The plastic closure of this invention includes a generally tubular portion and a portion which is deformed radially or crimped into the reduced diameter portion of the container to retain the closure on the container and as a cap to seal the open end of the container. The plastic closure of this invention may also be used as a cap or collar with a conventional vial and elastomeric stopper In the preferred embodiment, the plastic closure of this invention is formed of a polymer which is sufficiently malleable to permit radial deformation, yet sufficiently rigid to retain its shape following deformation and sufficiently resistant to creep to maintain the seal between the plastic cap and the container following radial deformation.

The preferred embodiment of the plastic closure of this invention is formed of a polymer alloy or melt blend which includes a relatively tough soft malleable copolymer and a relatively rigid polymer. In the most preferred embodiment of the plastic closure of this invention, the composite polymer is a polymer alloy of a relatively soft malleable co-polymer and a relatively rigid polymer. The preferred relatively rigid polymer is a polyamid or a polycarbonate and the preferred relatively soft co-polymer may be selected from polyesters or polyolefins. The resultant polymer alloy or composite preferably has an elongation at yield between 5% and 10% and an elongation at break greater than 100% with a flectural modulus of greater than 1900 MPa.

Where the container includes a radial rim portion adjacent the open end, the plastic closure of this invention includes a generally cylindrical tubular portion preferably having an internal diameter generally equal to or slightly greater than the external diameter of the rim portion of the container adapted to be received over the rim portion of the container having a free distal end adapted to be deformed radially inwardly or crimped beneath the rim portion of the container and sealed relation. The plastic cap or collar of this invention may also include a radially inwardly projecting proximate portion which overlies the rim portion of the container and/or the stopper. This radial portion may be closed or more preferably includes a central opening which may be closed with a flip-off or peel-off type plastic closure or seal. In the preferred embodiment, the peel-off seal includes a looped end portion which is welded or glued to the tubular portion surrounding the transferset providing indication of tampering and a free end which may be gripped to remove the seal.

Where the plastic collar of this invention is utilized to secure a transferset for transferring fluid from the container to a second container, the preferred embodiment of the collar includes a second tubular portion which at least partially surrounds the internal components of the transferset. In one preferred embodiment, the second tubular portion completely surrounds the internal components of the transferset, which may have a closed end integral with the second tubular portion or closed with a sealing member. In the most preferred embodiment, the collar portion is integral with the tubular portion surrounding the transferset and the tubular fluid transfer portion such that the major components of the transferset may be molded in one piece. In another embodiment, the transferset includes a cup-shaped cap which is received over the second tubular portion of the collar. In the preferred embodiments of the plastic collar of this invention which secures or is integral with a transferset attached to the container, the internal surface of the tubular portion which surrounds the rim of the container includes an annular resilient ring which is biased against the rim portion of the container to prevent rotation of the collar and transferset on the vial. In one preferred embodiment, the internal surface of this tubular portion includes an annular groove adjacent the free end of the tubular portion and the annular resilient ring is received and retained in the annular groove. The preferred embodiment of the plastic closure of this invention may also be formed of a relatively clear polymer or polymer alloy which maintains its clarity under the stress of deformation which is particularly advantageous where the plastic closure of this invention is utilized as a collar to secure and seal a transferset on the container.

The method of this invention then includes forming a plastic closure having a generally cylindrical tubular portion having an internal diameter generally equal to or slightly greater than an outside diameter of the rim portion of the container and an integral radial rim portion, disposing the closure over the rim of the container with the radial rim portion overlying the rim portion of the vial and the tubular portion surrounding the container rim, and then radially permanently deforming or crimping the free end of the tubular portion of the collar into the neck portion of the container, beneath the rim portion, permanently securing the closure on the container and sealing the container open end. In the most preferred embodiment of the method of this invention, the plastic closure of this invention is formed by injection molding the plastic closure from a polymeric alloy or composite having a relatively soft malleable polymer or co-polymer and a relatively rigid polymer, wherein a polymeric alloy or composite is formed during the injection molding. Where a resilient or polymeric ring is utilized to prevent rotation of the closure on the container, the ring may be co-injected with the polymer forming the closure or an annular groove may be formed in the tubular portion of the closure, adjacent the free end. The method then includes inserting the annular resilient ring in the groove prior to radial permanent deformation of the free end of the closure as described, such that the resilient ring is biased against the rim portion of the container. A thermoplastic elastomer may also be co-injected with the polymer forming the closure to form a coating or film on the inside surface of the closure which is integrally bonded to the polymer of the cap.

The plastic closure of this invention may be utilized with a vial or other medical container having a conventional elastomeric stopper or as a collar in combination with a transferset having a sealing member as disclosed in the prior art or more preferably the collar portion may be formed integral with components of the transferset. Where the plastic closure of this invention is used to seal a container having an elastomeric stopper, the proximate radial lip of the closure is received over and preferably biased against the resilient radial lip of the stopper during radial deformation or crimping of the free of the tubular portion of the closure beneath the rim of the container. The plastic closure of this invention thus eliminates the problems associated with malleable metal collars or caps, such as aluminum, and is relatively inexpensive, and simple to manufacture, particularly when compared with aluminum caps having a protective coating. The plastic closure of this invention assures an excellent seal of the container and can be injection molded in a clean environment or washed, if necessary. Finally, the plastic closure of this invention accommodates the tolerances of the vial and particularly the buildup of tolerance variations in the combination of a conventional vial and elastomeric stopper. Other advantages and meritorious features of the present invention will be more fully understood from the following description of the preferred embodiments, the appended claims and the drawings, a brief description of which follows.

BRIEF DESCRIPTION OF THE DRAWINGS

FIG. 4 is a partial side view of an alternative embodiment of the plastic closure of this invention assembled on a vial or other container;

FIG. 5 is a top cross-sectional view of FIG. 4 in the direction of view-arrows 5—5;

FIG. 6 is a side view of a vial and transferset assembly having the plastic collar of this invention;

FIG. 7 is a partial side cross-sectional view of an alternative embodiment of the vial and transferset assembly;

FIG. 8 is a partial side cross-sectional view of the vial, collar and transferset assembly similar to FIG. 7 of an alternative embodiment of this invention;

DETAILED DESCRIPTION OF THE PREFERRED EMBODIMENTS

Figure 1:
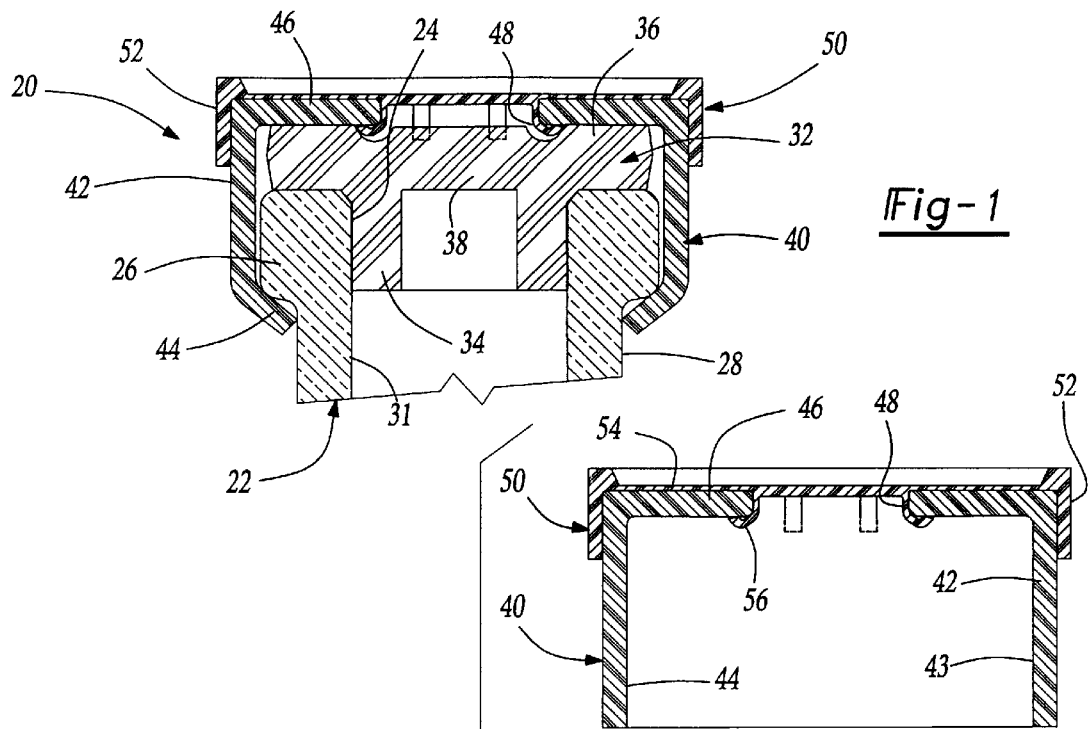
FIG. 1 is a side cross-sectional view of one preferred embodiment of the plastic closure of this invention secured to and sealing a conventional vial having an elastomeric stopper.
Figure 2:
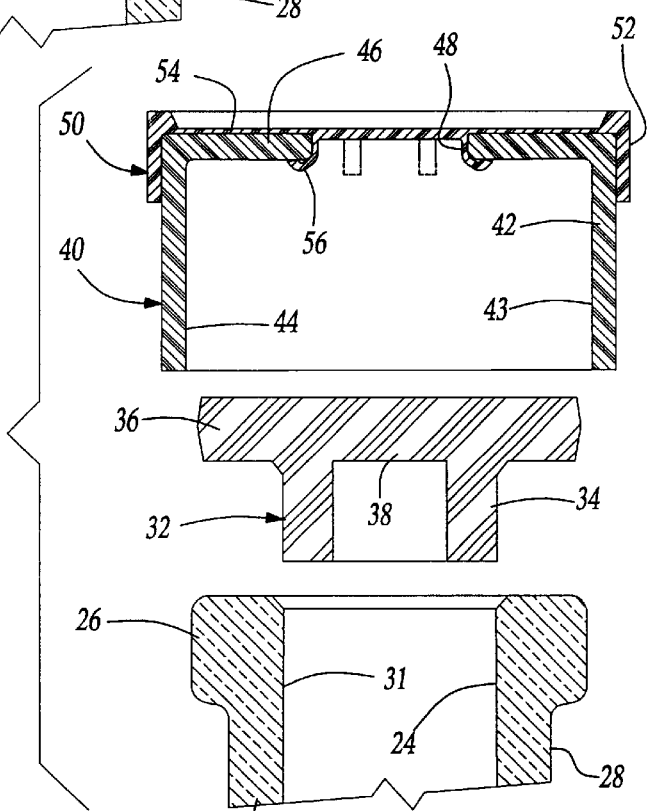
FIG. 2 is an exploded side cross-sectional view of the open end of a conventional vial, elastomeric stopper and the plastic closure shown in FIG. 1 prior to radial deformation of the free end of the closure.
Figure 3:
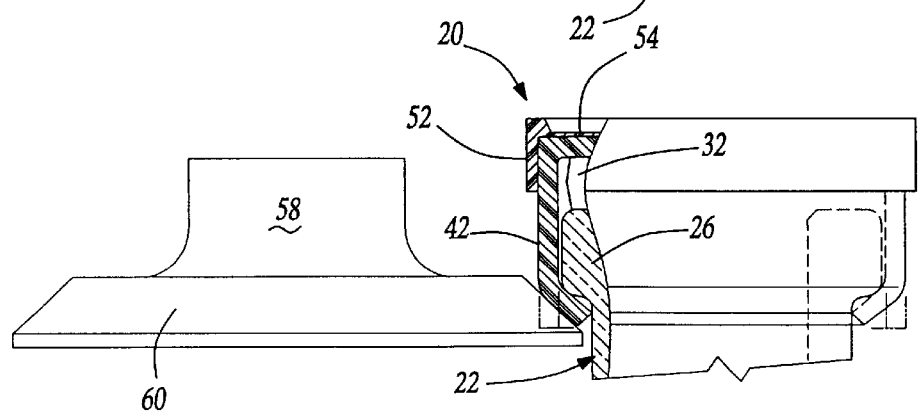
FIG. 3 is a side partially cross-sectioned view of the assembly shown in FIG. 1 illustrating radial deformation or crimping of the closure.
Figure 9:
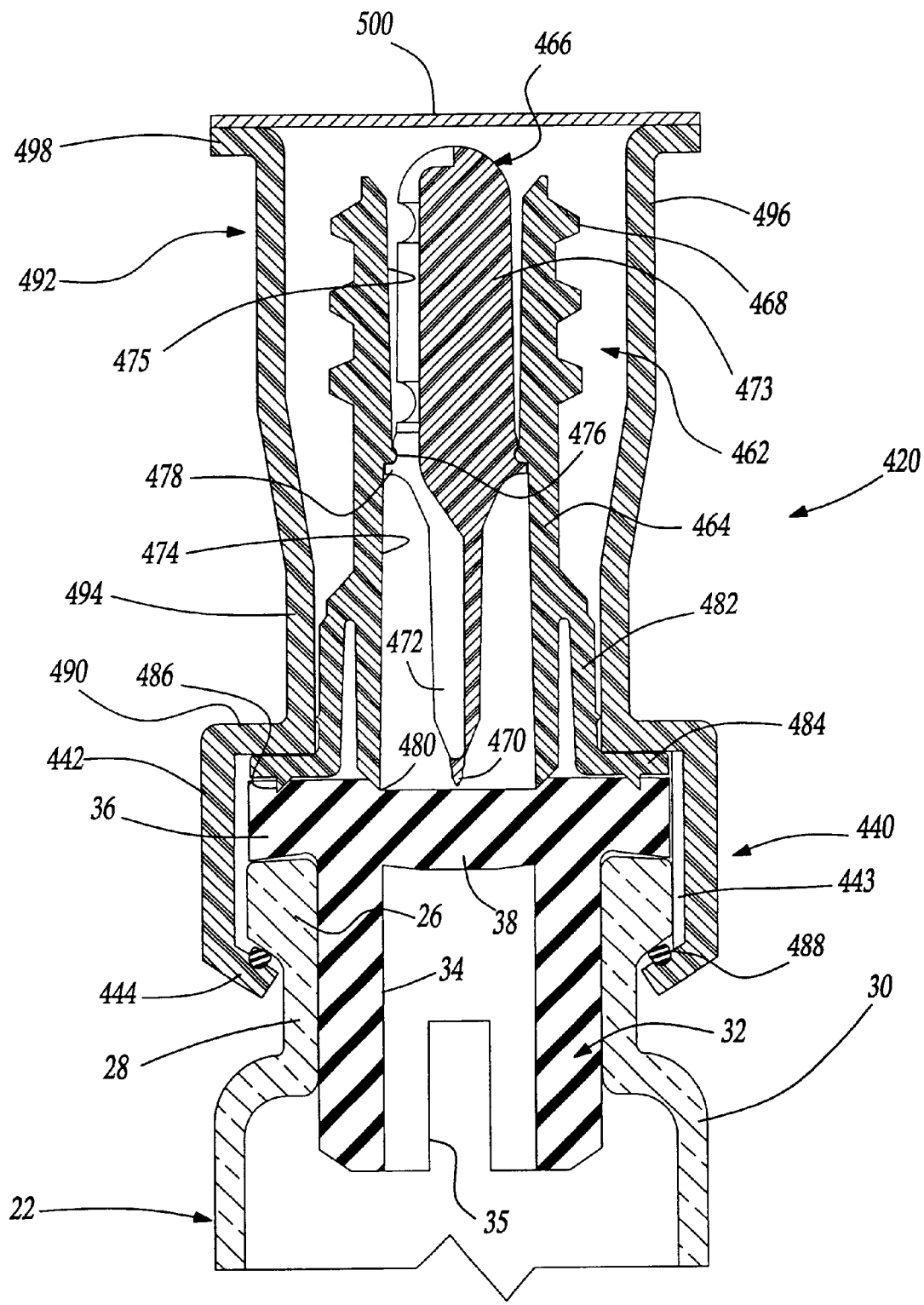
FIG. 9 is a partial side cross-sectional view of a vial, stopper and transferset assembly of this invention.
Figure 10:
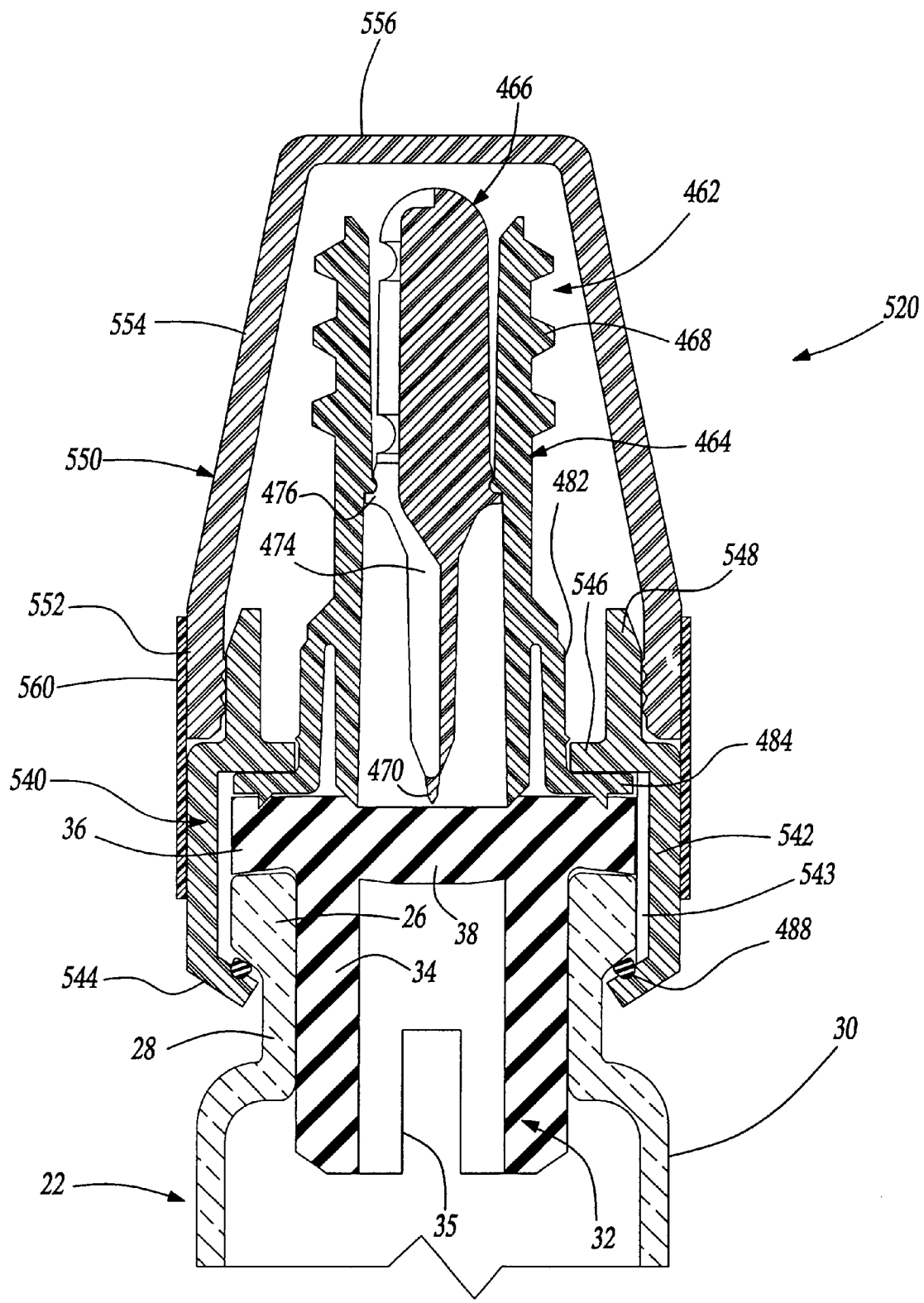
FIG. 10 is a partial side cross-sectional view illustrating a further alternative embodiment of the vial and transferset assembly of this invention.

FIGS. 1 to 3 illustrate one preferred embodiment of the vial, stopper and cap assembly 20 of this invention. As set forth above, the closure of this invention may be utilized to seal various containers and is particularly useful for sealing medicament containers such as the conventional vial 22 illustrated in FIGS. 1 to 3. The vial includes an open end 24, an annular radially extending rim portion 26 and a neck portion 28 adjacent the rim portion. As best shown in FIGS. 9 and 10, the neck portion 28 of the vial has a reduced diameter when compared to the rim portion 26 and the container portion 30. The internal surface 31 of the vial adjacent the open end 24 is generally cylindrical. Medicament vials of this type are generally formed of glass or a sterilizable plastic. The open end 24 of the vial is typically closed with an elastomeric stopper 32 having a tubular body portion 34 which is received in the open end 24 of the vial and a planar rim portion 36 which overlies the rim portion 26 of the vial as shown in FIG. 1. The stopper is generally formed of a resilient elastomeric material such as synthetic or natural rubber. The central portion 38 of the planar rim portion 36 may be pierced with a hypodermic needle, for example, to either withdraw fluid from the vial or add a solvent or diluent to the vial where the medicament in the vial is a dry or powder drug. The tubular portion 34 of the stopper has an external diameter generally greater than the internal diameter of the internal cylindrical surface 31 of the vial to provide a tight or interference fit.

One preferred embodiment of the closure 40 is shown in FIG. 1 attached to a vial 22 and stopper 32 assembly, prior to assembly in FIG. 2 and during assembly in FIG. 3. This embodiment of the collar 40 includes a tubular portion 42 which surrounds the rim portion 26 of the vial and the planar rim portion 36 of the stopper. Where the external surface of the rim portion 26 of the vial is cylindrical, the tubular portion 42 of the collar will generally also be cylindrical. As shown in FIG. 1, the free end 44 of the tubular portion 42 is deformed inwardly or crimped beneath the adjacent surface of the rim portion 26 of the vial, permanently securing the collar 40 on the vial and sealing the vial. This embodiment of the collar 40 also includes an integral radial proximate portion 46 which overlies the rim portions 26 and 36 of the vial and stopper, respectively. The radial portion 46 is preferably integral with the tubular portion 42 of the collar. This embodiment of die collar 40 also includes a central opening 48 which overlies the central portion 38 of the stopper, preferably coaxially aligned with the central portion of the stopper As described below, however, the central opening 48 may be eliminated in certain applications of this invention. As used herein, the terms proximate and distal are used solely for ease of description, wherein the term proximate refers to elements or portions of elements closest to the rim portion 36 of the stopper and distal refers to elements or portions of elements more remote from the rim portion of the stopper. Further, the terms cap and collar are sometimes used herein interchangeably. The term cap, however, generally refers to a closure having a radial portion which overlies the container opening and collar is used to refer to a closure used to secure an element, such as a transferset, to the container.

In this disclosed embodiment, the collar 40 includes a shallow cup-shaped cap 50. In the disclosed embodiment, the cap 50 includes a tubular portion 52 which surrounds the proximate portion of the tubular portion 42 of the collar, an integral central radial bridging portion 54 and a plurality of U-shaped tabs which, in the disclosed embodiment, are integral with the central bridging portion 54. The U-shaped tabs 56 are received through the central opening 48 of the collar and snap in place to securely retain the cap 50 on the collar 40. As shown in FIG. 2, the cap 50 may be preassembled on the collar 40 prior to assembly of the collar on the vial. The tabs 56 may also be separate members or the central portion of the cap 50 including the tabs 56 may be a separate member.

The collar 40 is then assembled on the vial 22 as shown in FIG. 2. In a typical application, the tubular portion 34 of the stopper is first inserted into the opening 24 of the vial 22 generally after the vial is filled. As set forth above, the plastic collar 40 of this invention may be used with various containers including conventional medicament vials as shown. Thus, in a typical application, the vial 22 will first be filled with a medicament. The tubular portion 42 of the collar 40 is then received over the rim portion 36 of the stopper and the rim portion 26 of the vial as shown in FIG. 3. The free end 44 (shown before deformation in phantom in FIG. 3) is then deformed radially beneath the radial rim 26 of the vial by a suitable tool, such as the crimping tool 58 shown in FIG. 3. The disclosed embodiment of the crimping tool includes a conical rim 60 which deforms or crimps the free end 44 of the collar beneath the rim 26 of the vial. In a typical application, the tool 58 is rotated around the rim 26 of the collar 40, deforming or crimping the free end 44 as shown in FIGS. 1 and 3. In certain applications, it may be desirable to heat either the free end 44 of the collar or the tool 58 to facilitate crimping. The sealed vial may now be stored for later use.

When the vial is ready for use, the cap 50 may be removed simply by forcing one side of the cap 50 upwardly away from the collar 40, removing the cap 50 from the collar 40 and exposing the central opening 48 of the collar and the central portion 38 of the stopper. The central portion 38 of the stopper may then be pierced with a conventional hypodermic needle, for example, providing access to the container portion 30 of the vial. Where the material of the cap 50 is selected to provide resiliency, such as polyethylene or polypropylene, the tabs 56 will bend under thumb pressure, permitting easy removal of the closure 50. Alternatively, where the material of the cap is relatively rigid, at least some of the tabs 56 will break also permitting removal of the cap. It should also be noted that the radial portion 46 of the collar is preferably compressed against the resilient rim portion 32 of the elastomeric stopper during radial deformation of the free end 44 of the collar to assure a secure seal of the vial following installation. The tabs 56 are thus compressed into the radial rim 32 of the stopper as shown in FIG. 1.

The polymer selected for the plastic closure of this invention can best be described by its required physical properties. The polymer must be sufficiently malleable to permit radial deformation or crimping, yet sufficiently rigid to retain its shape following deformation. The polymer must also be sufficiently resistant to creep to maintain the seal between the plastic cap and the container following radial deformation. It has been found that a polymer having an elongation at yield between 5% and 10% and an elongation at break greater than 100%, combined with a flexural modulus of greater than 1,900 MPa has superior performance. Where the plastic closure of this invention is utilized for sealing vials containing a medicament, the polymer should also be sterilizable and, in certain applications such as the plastic collar for a vial transferset described below, the polymer is preferably relatively clear and maintains its clarity under the stress of deformation or crimping. It has been found that certain polymer alloys or composite polymers including melt blends or alloys and co-polymers having polymers of different malleability and rigidity are preferred in many applications. That is, the plastic closure of this invention is preferably formed of a polymer alloy, composite polymer or co-polymer including a relatively rigid polymer and a tough relatively soft malleable co-polymer. The most preferred polymer is a polymer alloy or melt blend including a polyamid or polycarbonate as the rigid polymer providing the strength and resistance to creep desired for this application. The relatively soft malleable co-polymer may be selected from various polymers including polyesters and polyolefins; however, a polymer alloy including a polycarbonate or polyamid and a polyester has been found particularly suitable for this application.

As will be understood, various polymeric melt blends, alloys, composites and co-polymers are being developed on a rapidly increasing basis and therefore the plastic collar of this invention is not limited to a specific polymer, provided the polymer has the desired physical properties described above. Suitable polymers for the plastic collar of this invention include EASTAR® MB polymers, which are melt blend and alloy polymers and EASTAR® thermoplastic polymers, which are neat polymers sold by Eastman Chemical Company of Kingsport, Tenn. and Eastman Chemical AG of Zug, Switzerland under the trade names "DA003, DN003" and "DN004". These materials are polymer melt blends, alloys and co-polymers of polycarbonate or polyamid and polyester. As used herein, the terms melt blends and alloys refer to polymeric compositions having two or more polymers of different physical properties or characteristics, such as the EASTAR® polymers of Eastman Chemical Company described above which include a polycarbonate or polyamid and a polyester. The polymer selected for the plastic collar of this invention may also include fillers and other constituents which would be more accurately described as a composite. Although the base polymers may still be a polymeric melt blend or alloy. As used herein, the term composite is used in its broadest sense to include alloys or melt blends, composites and co-polymers. As will be understood, the manufacturer or supplier of the raw material will normally blend the polymers based upon the specifications of the customer. The polymers may be co-injected to form a polymeric melt blend, alloy or composite or formed by any other suitable processes. It is anticipated, however, that other polymers having the described physical characteristics may also be utilized in the plastic collar or cap of this invention. In certain applications, it may also be desirable to coat at least the interior surface 43 of the collar shown in FIG. 2 with a thermoplastic elastomer, or the entire collar may have a thin layer of a thermoplastic elastomer. The thermoplastic elastomer coating may be applied as a film or by co-injection with the polymer forming the collar 40. The collar 40 and the closure 50 may be formed by conventional injection molding processes.

The plastic collar 140 of the vial, stopper and collar assembly 120 shown in FIGS. 4 and 5 may be identical to the collar 40 shown in FIGS. 1 to 3 except that the collar 140 includes a plurality of ribs 162 which provide an improved finger gripping surface for removal of the cap or closure 50. The vial 22, elastomeric stopper 32 and the cap or closure 50 are identical to the same elements in FIGS. 1 to 3 and are therefore numbered the same. The collar 140 is numbered in the same numerical sequence as the collar 40 in FIGS. 1 to 3 for ease of reference. As described above, the cap or closure 50 may be eliminated in certain applications in either embodiment by either providing an integral frangible central portion or by applying a peel-off seal of paper, plastic, aluminum or foil over the radial portion 46 adjacent the central opening 48 having a suitable adhesive providing a microbio barrier sealing the central opening 48.

FIG. 6 illustrates one embodiment of the plastic collar or cap 240 of this invention mounted on a conventional vial 22 having a container portion 30 utilized to secure a fluid transferset 250. The plastic collar 240 of this invention may be utilized to secure any fluid transferset to a suitable container, such as the conventional vial 22 shown in FIG. 6 including but not limited to the fluid transferset disclosed in co-pending application Ser. No. 09/031,302 filed Feb. 26, 1998, the disclosure of which is incorporated herein by reference. The plastic collar 240 of this invention includes a tubular portion 242 and a free distal end 244 which is deformed radially or crimped beneath the rim portion 26 of the vial 22 as described above and shown in FIGS. 7 and 8. In the embodiment of the vial and transferset assembly 220 shown in FIG. 6, the collar includes a radial portion 246 and a second tubular portion 248 integral with the radial portion 246 having a diameter less than the tubular portion 242. In this embodiment, the fluid transferset 250 includes a cup-shaped cap or closure 252 having a proximate radial portion 250 as shown in FIGS. 7 and 8 which is received between the radial portion 246 of the collar which overlies the rim portions of the elastomeric stopper and the vial secured in place by the plastic collar 240.

FIGS. 7 and 8 illustrate alternative embodiments of the collar assembly shown in FIG. 6 which include an elastomeric or rubber element limiting rotation of the collar on the vial. In the embodiment of the collar 240 shown in FIG. 7, the distal free end 244 of the tubular portion 242 includes a groove 264 in the internal surface 243 which receives a rubber or an elastomeric O-ring 268. Thus, when the free end 244 is deformed radially inwardly or crimped against the underside of the rim portion 26 of the vial, the O-ring 268 is resiliently deformed against the rim portion 26 providing torque resistance to turning of the collar 240 relative to the vial. In one embodiment of the fluid transferset, the cap 252 is removed prior to use by twisting the cap which is provided with a frangible portion 270 formed by the V-shaped groove 272 located beneath the tubular portion 248. The frangible connection between the distal portion of the cup-shaped cap 248 and the proximate portion including the radial flange 252 may take various forms, including, for example, a V-shaped continuous or discontinuous groove in the inner or outer wall of the cap. Thus, it is desirable to increase the torque required to turn the collar 240 relative to the vial which is provided by the O-ring 268. In addition, the O-ring provides an additional seal preventing contamination of the space between the collar and the vial. Thus, the O-ring 268 or the seal disclosed in FIG. 8 may be added to the embodiments of the plastic collar shown in FIGS. 1 and 4. In the embodiment of the collar assembly 340 shown in FIG. 8, the O-ring has been replaced with an annular sealing member 368 which, in the disclosed embodiment, is flat or generally rectangular. The annular sealing member 368 shown in FIG. 8 may be formed of a suitable elastomeric material, such as natural or synthetic rubber, which is co-injected with the polymer forming the collar 240 or 340 or secured to the internal surface 243 or 343 of the free end 244 or 344 of the tubular portion of the collar by a suitable adhesive. The common elements of the vial, stopper and transferset shown in FIGS. 6, 7 and 8 are numbered the same and the collar 240 and 340 are numbered in the same numerical sequence for ease of reference.

FIGS. 9 and 10 illustrate alternative embodiments of the plastic collar of this invention utilized to secure a vial transferset as described more fully in the above-referenced co-pending patent application, wherein the plastic collar forms a part or component of the transferset. Again, the vial 22 may be identical to the medicament vial described above or other suitable container. The elastomeric stopper 32 may be identical to the elastomeric stopper described above except that in this embodiment, the tubular portion 34 of the stopper includes conventional axial slots 35 which permit freeze drying of liquid in the vial 22.

The components of the vial fluid transferset disclosed in the above-referenced patent application need not be described herein in detail. Briefly, the fluid transfer assembly or transferset 462 includes a tubular transfer member 464 and a piercing member 466. The tubular transfer member 464 includes a Luer connection 468 which in the disclosed embodiment are male threads on the exterior surface of the tubular transfer member. The piercing member 466 includes a pointed piercing end 470 and an external channel 472 which, in the disclosed embodiment, extends from adjacent the piercing end 470 to the body or barrel portion 473. The external channel 472 may be continuous and extend longitudinally as shown or extend spirally or be discontinuous. The tubular transfer member 464 includes a proximate internal surface 474 and a distal internal surface 475 having a diameter less than the internal diameter of the proximate internal surface 474 to define a lip 476 which receives the radial flange 478 of the piercing member 466, such that the piercing member 466 is retained in the tubular transfer member 466 for telescopic movement of the piercing member toward the central portion 38 of the elastomeric stopper 32. The proximate end of the tubular transfer member 464 in the disclosed embodiment includes a relatively sharp edge 480 which is pressed into the central portion 38 of the elastomeric stopper during assembly as described below and includes an integral outer tubular portion 482 having a radial lip 484 which includes an annular barb 486 which is pressed into the radial rim portion 36 of the stopper.

The plastic collar 440 of this embodiment of the invention includes a tubular portion 442 which surrounds the planar rim portion 36 of the stopper and the radial rim 26 of the vial. In this embodiment, however, the internal surface of the tubular portion 442 has a plurality of longitudinal ribs 443 which engage the planar portion 36 of the stopper and the rim 26 of the container and retains the collar on the container following preassembly. In the disclosed embodiment, the collar includes three ribs 443 spaced equally along the tubular portion 442; however, the number may be varied as desired. The free end 444 is deformed radially inwardly or crimped around the rim portion 26 of the vial as described above which includes an elastomeric O-ring 488 which limits rotation of the collar 440 on the vial 22. The collar 440 further includes a radial portion 490 integral with the tubular portion 442 which overlies the rim portions 36 and 26 of the elastomeric stopper and vial, respectively and 484 of the transferset 462. The collar 440 further includes a tubular portion which is integral with the radial portion 490, which surrounds the transferset 462. In this embodiment, the distal tubular portion 496 has an internal diameter greater than the internal diameter of the proximate tubular portion 494 to more easily accommodate receipt of a syringe or intravenous (IV) set connector during use of the transferset. In the disclosed embodiment, the distal end of the collar includes a radial flange 498 and the distal open end of the collar is sealed with a peel-off seal 500 formed of paper, plastic, aluminum or foil which is adhesively bonded to the radial flange portion 498 providing easy access to the transferset 462.

The plastic collar and transferset assembly of this invention shown in FIG. 9 may be utilized to transfer fluid between the vial 22 or other suitable container and a conventional syringe, intravenous set or the like. The seal is removed by removing the peel-off seal 500 which provides access to the transferset 462. A conventional syringe (not shown) having a female Luer Lock connector, for example, may be threaded on the male Luer Lock connector 468. As the Luer connectors of the tubular transfer member 464 and syringe are threaded together, the, nozzle portion of the syringe is received in the tubular transfer member which simultaneously drives the piercing end 470 of the piercing member 466 through the central portion 38 of the elastomeric stopper providing fluid communication between the vial 22 and the interior of the tubular transfer member 464 through external channel 472. In a typical application, drugs in a dry or powdered form may be stored in the vial 22 to increase the shelf life of the drug. The syringe may be utilized to transfer a diluent or solvent into the vial to reconstitute the drug which may then be withdrawn into the syringe for application to a patient.

FIG. 10 illustrates a further alternative embodiment of the plastic collar and transferset of this invention wherein the entire cap is removable. The transferset 462 including the tubular transfer member 464 and piercing member 466 may be identical to the transferset disclosed in FIG. 9. Further, the vial 22 and elastomeric stopper 32 are conventional as shown in FIG. 9.

The embodiment of the plastic collar 540 shown in FIG. 10 includes a tubular portion 542 which surrounds the planar rim portion 36 of the stopper having internal longitudinal spaced ribs 543 which receives the rim portion 26 of the vial to assure preassembly of the components on the vial prior to crimping. The free end 544 of the collar is deformed radially or crimped beneath the rim portion 26 of the stopper as described above. The internal surface of the free end 544 of the collar further includes an elastomeric O-ring 488 as described above which is resiliently deformed against the rim portion 26 of the vial preventing rotation of the collar on the vial. In this embodiment of the plastic collar 540, the radial portion 546 overlies the radial portion 484 of the tubular transfer member and the tubular portion 548 is spaced inwardly from the tubular portion 542 to receive a cup-shaped cap 550. As shown, the cup-shaped cap 550 includes a cylindrical proximate portion 552, a conical portion 554 and a closed end portion 556. In this embodiment, the cap 550 is secured to the plastic collar 540 by a twist-off preslit label 560 made of plastic, aluminum or foil which provides evidence of tampering. The cap 550 may then be easily removed by breaking or rupturing the seal 560 providing access to the transferset 462.

Figure 11:
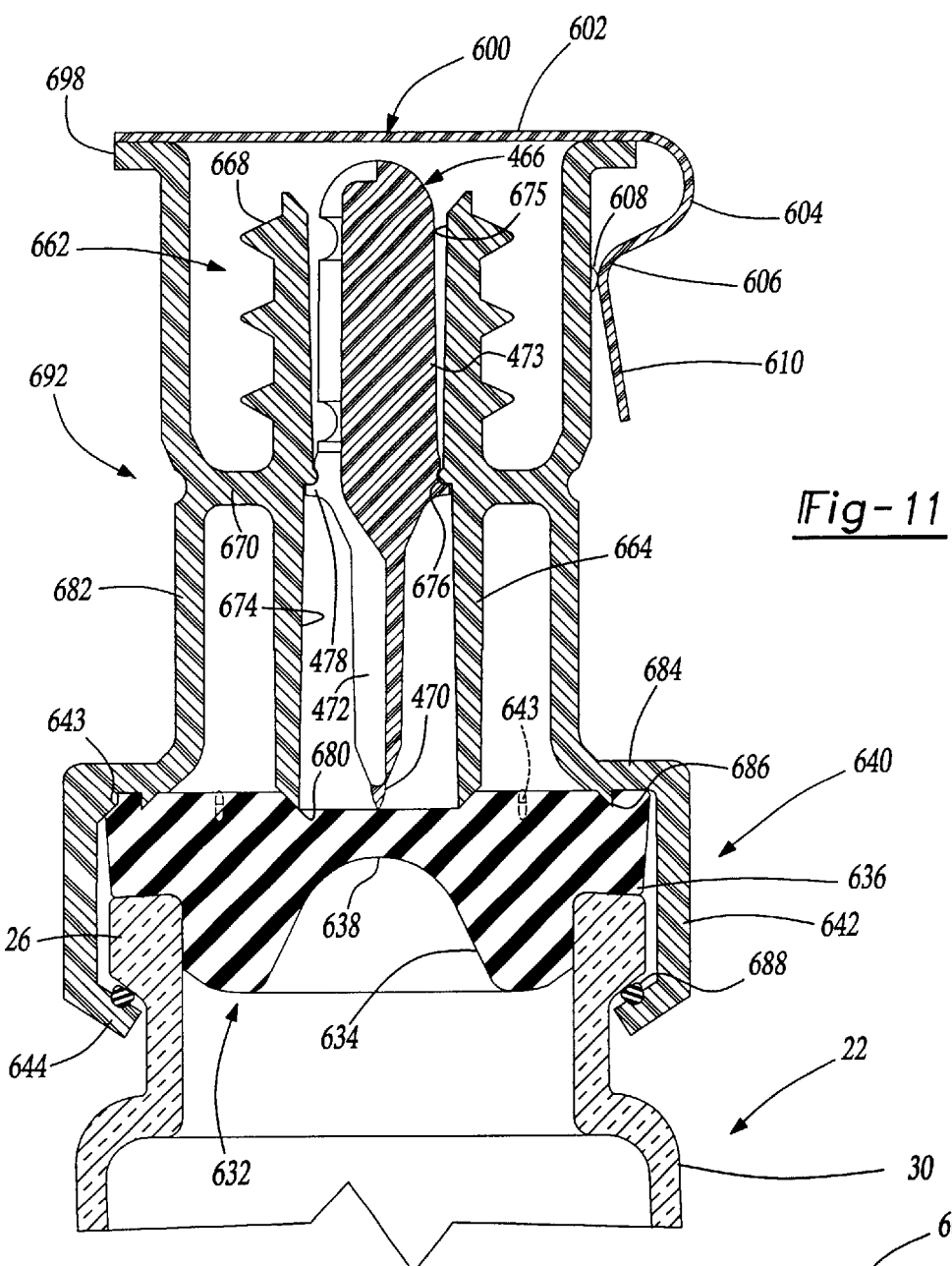
FIG. 11 is a side cross-sectional view of an embodiment of a collar and transferset assembly similar to FIG. 9 which has been simplified to reduce costs.

The plastic collar 640 as shown in FIG. 11 is similar to the collar and transferset assembly shown in FIG. 9 except that the tubular transfer member 664 is formed integral with the outer tubular portion 682 thereby simplifying the design and permitting molding of these parts of the transferset in one piece, which also simplifies assembly and reduces the cost. The components of the integral collar and transferset assembly of FIG. 11 has been numbered where practical in the same sequence as the collar and transferset assembly of FIG. 9. Briefly, the transferset 662 includes a tubular transfer member or portion 664 and a piercing member 466 which in this embodiment is identical to the piercing member 466 shown in FIG. 9 and described above. The tubular member 664 includes a Luer Lock connection 668 which in the disclosed embodiment are male threads on the exterior surface of the tubular transfer member. As described above, the tubular transfer member or portion 664 includes a proximate internal surface 674 and a distal internal surface 675 having a diameter less than the internal diameter of the proximate internal surface 764 to define a lip 676 which receives the radial flange 478 of the piercing member 466, such that the piercing member 466 is retained in the tubular transfer portion 664 for telescopic movement of the piercing member toward the central portion 638 of the stopper 632. In this embodiment, the elastomeric stopper 632 includes a planar portion 636 which is received on the rim 26 of the vial 22 as described above; however, in this embodiment of the stopper 632, which is also conventional, the generally tubular portion 634 which extends into the internal surface 31 of the vial is thicker and the internal surface is arcuate defining an arcuate central portion 638 which receives the piercing end 470 of the piercing member 466.

The proximate end of the tubular transfer portion 664 in the disclosed embodiment also includes a relatively sharp edge 680 which is pressed into the central portion 638 of the elastomeric stopper during assembly as described above. The plastic collar 640 of this embodiment includes a tubular portion 642 which surrounds the planar rim 636 of the elastomeric stopper and the radial rim 26 of the vial. In this embodiment, however, the internal surface of the tubular portion 642 and the radial portion 684 includes a plurality of spaced ribs 643 which are pressed into the planar portion 636 of the elastomeric stopper, preventing rotation of the collar 640 and transferset on the vial. As described above, the integral collar and transferset is permanently secured to the vial by permanently radially deforming the free end 644 inwardly around the rim portion 26 of the vial which includes an elastomeric O-ring 688 which also limits rotation of the collar 640 on the vial 22 and an additional seal of the assembly. The outer tubular portion 682 is formed integral with the tubular transfer portion 664 by an integral radial annular web 670 forming a rigid assembly which is simpler in design and less costly as described above. The radial portion 684 of the outer tubular portions 682 includes an annular barb 686 having the same function as the barb 486 described above. Other details of the preferred embodiment of the integral collar and transferset assembly shown in FIG. 11 will be understood from the description above. As will be understood by those skilled in the art, however, the integral design of the collar 640, outer tubular member 682 and the tubular transfer member 664 may be injection molded in one piece forming a relatively rigid structure which eliminates assembly of the individual components and reduces costs.

Figure 12:
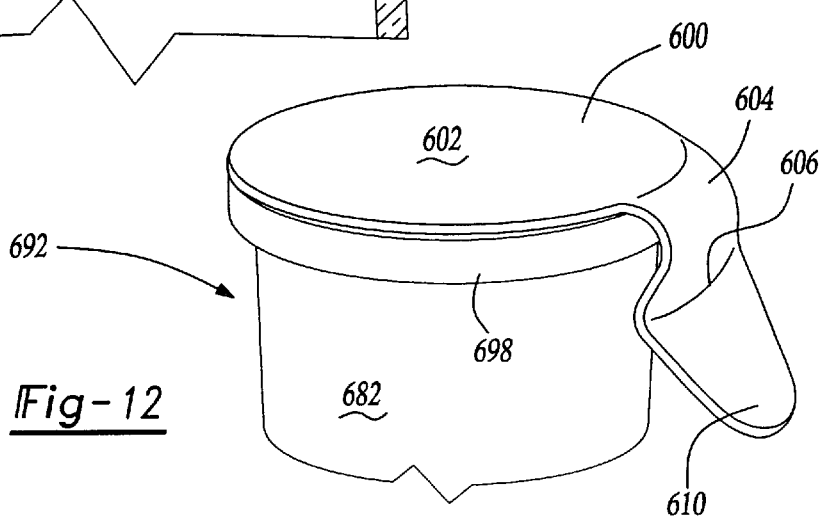
FIG. 12 is top perspective view of the transferset shown in FIG. 11 illustrating a preferred embodiment of the peel-off seal.

The peel-off seal 600 shown in FIGS. 11 and 12 seals the internal components of the transferset 662, may be easily removed and provides an indication of tampering. The disclosed embodiment of the seal 600 includes a sealing portion 602 which in the disclosed embodiment is circular to accommodate the shape of a conventional vial and may be formed of paper, plastic, aluminum or foil which is adhesively bonded to the radial flange portion 698 of the outer tubular portions 682 as described above. This embodiment, however, includes an integral tab 604 including a central portion 606 which is welded or adhesively bonded to the outer tubular portion 682 of the transferset by glue 608. Securing the central portion 606 of the seal to the transferset prevents inadvertent removal of the seal and evidence of tampering. The free end 610 of the tab may be easily gripped for peeling off the seal 600 from the transferset.

As described in regard to the embodiments of the plastic cap shown in FIGS. 1 to 5, the plastic collar 440 in FIG. 9, 546 in FIG. 10 and 640 in FIG. 11 are preferably secured to the vial 22 by compressing the radial portion 490 in FIG. 9, 546 in FIG. 10 or 684 in FIG. 11 against the resilient planar portion of the stopper. In the embodiments shown in FIGS. 9 and 10, the radial portion 490 in FIG. 9 or 546 in FIG. 10 is compressed against the radial portion 484 of the tubular transfer member, which compresses the radial portion and the annular barb 486 against the resilient planar rim portion 36 of the elastomeric stopper during radial deformation of the free end 444 in FIG. 9 and 544 in FIG. 10 of the collar beneath the rim 26 of the vial, thereby sealing the vial and securing the collar to the vial. In the simplified embodiment of the integral collar and transferset shown in FIG. 11, the radial portion 684 of the outer tubular portion 682 of the transferset is compressed directly against the planar portion 636 of the resilient elastomeric stopper, which compresses the annular barb 686 against the planar rim portion 636 of the stopper during radial deformation of the free end 644 of the collar portion 640 forming a tight seal. The plastic collar 440 and the integral outer tubular portion 494 in. FIG. 9, 540 in FIG. 10 and the integral collar 640, outer tubular portion 682 and tubular transfer portion 664 are preferably formed of a polymer having the physical properties and characteristics described above, thereby permitting crimping of the collar on a vial or other container. More preferably, the plastic collar is formed of a polymeric melt blend or alloy including a tough relatively soft malleable polymer and a relatively rigid polymer and most preferably a polymeric alloy including polycarbonate and polyester. As will be understood, however, various modifications may be made to the plastic closure of this invention within the purview of the appended claims.

What is claimed is:

1. A sealed medical container and transferset assembly, said medical container having an open end, a rim portion surrounding said open end, a neck portion adjacent said rim portion having a diameter smaller than said rim portion, and a pierceable closure located in said open end of said medical container; said transferset comprising:

an integral generally tubular polymeric collar member having a first tubular portion surrounding said rim portion of said medical container including a free end permanently deformed radially inwardly into said neck portion and permanently securing said collar member to said medical container, a radial portion overlying said rim portion of said medical container and supported by said medical container rim portion and a second tubular portion generally coaxially aligned with said first tubular portion extending from said rim portion of said medical container and coaxially aligned with said open end of said medical container having an open end, said integral tubular polymeric collar member formed of a polymer which is sufficiently malleable to permit radial deformation, yet sufficiently rigid to retain its shape following deformation and sufficiently resistant to creep to maintain a seal between said collar and said medical container;

a closure overlying said open end of said second tubular portion of said collar member and secured thereto in sealed relation; and a piercing member telescopically supported within said second tubular portion and moveable relative to said second tubular portion to pierce said pierceable closure in said open end of said medical container to provide fluid communication between said medical container and said transferset.

2. The sealed medical container and transferset assembly defined in claim 1, wherein said transferset further includes a tubular transfer member located within said second tubular portion of said collar member coaxially aligned with said open end of said sealable closure of said medical container sealingly engaging said sealable closure and telescopically receiving said piercing member.

3. The sealed medical container and transferset defined in claim 2, wherein said tubular transfer member is integral with said second tubular portion of said collar member.

4. The sealed medical container and transferset assembly defined in claim 2, wherein said tubular transfer member includes a free distal open end having a Luer Lock connector for receipt of a Luer Lock connector of a second container.

5. The sealed medical container and transferset assembly defined in claim 1, wherein said polymeric collar member is formed of a polyamid polymer or a composite polymer including a relatively soft malleable co-polymer and a relatively rigid polymer.

6. The sealed medical container and transferset assembly defined in claim 1, wherein said free end of said first tubular portion includes an annular resilient ring retained on an internal surface of said collar member adjacent said free end biased against said medical container rim portion and preventing rotation of said collar member on said medical container.

7. A sealed vial and transferset assembly comprising a vial having an open end, a radial rich portion surrounding said open end and a reduced diameter neck portion adjacent said rim portion and a pierce closure located with said vial open end sealing said vial, and a transferset mounted on said vial open end of said vial for transferring fluid between said vial and a container, said transferset including a tubular transfer member having a first open end engaging said pierceable closure in sealed relation and a second open end, a piercing member reciprocally supported within said tubular transfer member and moveable relative to said tubular transfer member to pierce said pierceable closure and establish fluid communication between said vial and said tubular transfer member, and a plastic collar having first a tubular portion surrounding said rim portion of said vial having a free end permanently deformed radially inwardly into said vial neck portion permanently retaining said collar on said vial aid a second integral tubular portion surrounding said tubular transfer member having an open end and a closure closing said open end of said second tubular portion of said collar, said plastic collar formed of a polymer which is sufficiently malleable to permit radial deformation, yet sufficiently rigid to retain its shape following deformation and sufficiently resistant to creep to maintain the seal between said collar and said vial following deformation.

8. The sealed vial and transferset assembly defined in claim 7, wherein said plastic collar is formed of a polyamid polymer or a composite polymer including a relatively soft malleable co-polymer and a relatively rigid polymer.

9. The sealed vial and transferset assembly defined in claim 8, wherein said plastic collar is formed of a polymer alloy comprising a relatively soft malleable co-polymer and polycarbonate as said relatively rigid polymer.

10. The sealed vial and transferset assembly defined in claim 7, wherein said tubular portion of said plastic collar includes an annular resilient ring retained on an internal surface of said collar adjacent said free end biased against said vial radial rim portion and preventing rotation of said collar on said vial.

11. The sealed vial and transferset assembly defined in claim 10, wherein said internal surface of said tubular portion includes an annular groove adjacent said free end and said resilient ring is received and retained in said annular groove.

12. The sealed vial and transferset assembly defined in claim 7, wherein said tubular portion of said plastic collar includes an elastomeric coating on an internal surface thereof integrally bonded to said internal surface.

13. The sealed vial and transferset assembly as defined in claim 7, wherein said tubular transfer member is integral with said plastic collar.

14. The sealed vial and transferset assembly as defined in claim 13, wherein said tubular transfer member is integrally joined to said second tubular portion of said collar in coaxial spaced relation by an integral radial web portion.

15. The sealed vial and transferset assembly as defined in claim 13, wherein said plastic collar includes an integral radial portion between said first and second integral tubular portions overlying said pierceable closure of said vial and engaging said pierceable closure in sealed relation.

16. The sealed vial and transferset assembly as defined in claim 7, wherein said plastic collar includes an integral radial portion between said first and second integral tubular portions and said tubular transfer member includes an integral radially outwardly extending portion adjacent said first open end extending between said plastic collar radial portion and said vial open end sealingly engaging said pierceable closure.

17. A sealed medical container and transferset assembly, said medical container having an open end, a rim portion surrounding said open end, a neck portion adjacent said rim portion having a diameter smaller than said rim portion, and a pierceable closure received in said open end of said medical container sealing said container, said transferset comprising:

an integral generally tubular polymeric collar member having a first tubular portion surrounding said rim portion of said medical container including a free end portion permanently deformed radially into said neck portion permanently securing said collar member to said medical container and a second tubular portion generally coaxially aligned with said first tubular portion extending from said rim portion of said medical container having an open end coaxially aligned with said open end of said medical container;

a tubular transfer member located within said second tubular portion of said collar member coaxially aligned with said open end of said container having a first open end sealing engaging said pierceable closure and a second open end having a connector portion for attachment to a second medical container; and a piercing member telescopically supported within said tubular transfer member and moveable relative to said tubular transfer member pierce said pierceable closure and providing fluid communication between said medical container through said tubular transfer member to said second medical container.

18. The sealed medical container and transferset defined in claim 17, wherein said fluid transfer member is integral with said second tubular portion of said collar member.

19. The sealed medical container and transferset assembly as defined in claim 17, wherein said second tubular portion of said tubular polymeric collar surrounds said tubular transfer member in generally coaxial spaced alignment and said collar member includes an integral radial portion between said first and second tubular portions supported by said rim portion of said medical container.

20. The sealed medical container and transferset assembly as defined in claim 19, wherein said tubular transfer member is integral with said plastic collar second tubular portion and said radial portion sealingly engages said pierceable closure.

21. The sealed medical container and transferset assembly as defined in claim 19, wherein said tubular transfer member includes an integral radially outwardly extending portion adjacent said first open end extending between said plastic collar radial portion and said vial open end sealingly engaging said pierceable closure.

* * * * *